(12) United States Patent
Murdock

(10) Patent No.: US 11,166,834 B2
(45) Date of Patent: *Nov. 9, 2021

(54) EXTERNAL SPINAL BRACE

(71) Applicant: Ryan C. Murdock, Austin, TX (US)

(72) Inventor: Ryan C. Murdock, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/178,855

(22) Filed: Nov. 2, 2018

(65) Prior Publication Data

US 2020/0289303 A1    Sep. 17, 2020

Related U.S. Application Data

(63) Continuation of application No. 15/054,917, filed on Feb. 26, 2016, now Pat. No. 10,206,805.

(60) Provisional application No. 62/277,287, filed on Jan. 11, 2016.

(51) Int. Cl.
*A61F 5/02*        (2006.01)

(52) U.S. Cl.
CPC .............. *A61F 5/028* (2013.01); *A61F 5/026* (2013.01)

(58) Field of Classification Search
CPC .......... A61F 5/028; A61F 5/024; A61F 5/026; A61F 5/03; A61F 5/01; A61F 2005/0167; A61F 5/022; A61F 5/048; A61F 5/05808; A61F 5/02
See application file for complete search history.

(56) References Cited

U.S. PATENT DOCUMENTS

| | | | |
|---|---|---|---|
| 4,144,881 A | 3/1979 | Chappell | |
| 5,685,831 A | 11/1997 | Floyd | |
| 6,213,968 B1 | 4/2001 | Heinz | |
| 7,316,660 B1 | 1/2008 | Modglin | |
| 7,654,973 B2 | 2/2010 | Firsov | |
| 7,766,850 B2 | 8/2010 | Simanovsky | |
| 8,235,924 B2 | 8/2012 | Bachmann et al. | |
| 8,409,122 B2 | 4/2013 | Cropper et al. | |

(Continued)

FOREIGN PATENT DOCUMENTS

| | | |
|---|---|---|
| DE | 19610018 | 10/1996 |
| JP | 2005349177 | 12/2005 |

(Continued)

OTHER PUBLICATIONS

NPL03_Supplementary European Search Report, Application No. 17738758.6, dated May 17, 2019, 7 pages.

(Continued)

*Primary Examiner* — Ophelia A Hawthorne

(74) *Attorney, Agent, or Firm* — Trop, Pruner & Hu, P.C.

(57) ABSTRACT

In some embodiments, a system and/or method may include an external spinal brace system. The system may include a plurality of support mechanisms including at least first and second support mechanisms. The first support mechanism may be coupled, during use, to the second support mechanism such that the first and second support mechanisms are inhibited from decoupling. In some embodiments, the system may include a coupling system. The coupling system may couple the plurality of support mechanisms to a subject such that the plurality of support mechanisms are positioned, during use, along at least a portion of the subject's spine. In some embodiments, the external brace system applies a posterior distraction force to the subject.

20 Claims, 4 Drawing Sheets

(56) References Cited

U.S. PATENT DOCUMENTS

| | | | |
|---|---|---|---|
| 10,206,805 B2* | 2/2019 | Murdock | ............... A61F 5/028 |
| 2008/0021357 A1 | 1/2008 | Firsov | |
| 2010/0016774 A1 | 1/2010 | Wong | |
| 2010/0168630 A1 | 7/2010 | Cropper et al. | |
| 2010/0268137 A1 | 10/2010 | Bachmann et al. | |
| 2011/0184325 A1 | 7/2011 | Kamran et al. | |
| 2015/0282974 A1 | 10/2015 | Kamenaga et al. | |
| 2015/0297387 A1 | 10/2015 | Thompson et al. | |
| 2017/0196722 A1 | 7/2017 | Murdock | |

FOREIGN PATENT DOCUMENTS

| | | |
|---|---|---|
| WO | 2007027573 | 3/2007 |
| WO | 2017123466 | 7/2017 |

OTHER PUBLICATIONS

NPL01_International Search Report and Written Opinion, Application No. PCT/US2017/012497, dated Mar. 17, 2017, 10 pages.
NPL02_International Preliminary Report on Patentability, Application No. PCT/US2017/012497, dated Jul. 17, 2018, 7 pages.
Non Final Office Action for U.S. Appl. No. 15/054,917 dated Jun. 13, 2018.
Notice of Allowance for U.S. Appl. No. 15/054,917 dated Oct. 5, 2018.
European Patent Office, Office Action dated Jun. 18, 2021 in European Patent Application No. 17738758.6 (6 pages).

* cited by examiner

EXTERNAL SPINAL BRACE

PRIORITY CLAIM

This application is a continuation of U.S. patent application Ser. No. 15/054,917 entitled "EXTERNAL SPINAL BRACE" filed on Feb. 26, 2016, which claims priority to U.S. Provisional Patent Application No. 62/277,287 entitled "EXTERNAL SPINAL BRACE" filed on Jan. 11, 2016, all of which is incorporated by reference herein.

BACKGROUND OF THE INVENTION

1. Field of the Invention

The present disclosure generally relates to correcting spinal disorders. More particularly, the disclosure generally relates to a method and support system for treatment of spinal disorders resulting in abnormal curvature or structure of the human spine.

2. Description of the Relevant Art

Scoliosis is a medical condition in which a person's spinal axis has a three-dimensional deviation. Other disorders associated with abnormalities in posture include, for example, cerebral palsy, scoliosis, paralyses, dystonia, and injuries of the spine and joints. Such disorders may have far-flung consequences for the entire musculoskeletal system. Effective treatment and rehabilitation of such problems require complex, global therapies that take into account and have an effect on the entire musculoskeletal system.

Several surgical and nonsurgical methods have been tried in an attempt to treat such disorders. Surgical methods which have been used are in general highly invasive and involve, for example, coupling multiple metal rods to a subject's spine using multiple screws. Such highly invasive surgical procedures typically require a long and arduous recuperation period.

Noninvasive methods are usually more desirable but depending on the condition being treated have either limited success or require highly restrictive and painful external braces. Current rigid braces put exterior forces on the ribs of a subject which in some instances can lead to rib deformities. There are some flexible braces available which allow more freedom of movement. However, none of the known external braces appear to provide a distraction force to the spine and specifically a posterior distraction force.

Therefore a system and/or method which facilitate treatment of structural disorders of the spine without invasive techniques or unnecessarily restrictive braces would be highly desirable.

SUMMARY

In some embodiments, a system and/or method may include an external spinal brace system. The system may include a plurality of support mechanisms including at least first and second support mechanisms. The first support mechanism may be coupled, during use, to the second support mechanism such that the first and second support mechanisms are inhibited from decoupling. In some embodiments, the system may include a coupling system. The coupling system may couple the plurality of support mechanisms to a subject such that the plurality of support mechanisms are positioned, during use, along at least a portion of the subject's spine. In some embodiments, the external brace system applies a posterior distraction force to the subject.

In some embodiments, a system and/or method may include an external spinal brace system. The system may include a plurality of support mechanisms including at least a first and a second support mechanisms. The first support mechanism may include a first coupling portion and a first and a second engaging member at a first end of the first support mechanism. The first support mechanism may include a first coupling opening and a first and second opening at the second end of the first support mechanism. The second end may be opposite to the first end of the first support mechanism. The second support mechanism may include a second coupling portion and a third and a fourth engaging member at a third end of the second support mechanism. The second support mechanism may include a second coupling opening and a third and fourth opening at the fourth end of the second support mechanism. The fourth end may be opposite to the third end of the second support mechanism. The first coupling portion of the first support mechanism may be positioned, during use, in the second coupling opening of the second support mechanism. The first and second engaging members of the first support mechanism may be positioned, during use, in the third and fourth openings respectively of the second support mechanism. The system may include a coupling system coupling the plurality of support mechanisms to a subject such that the plurality of support mechanisms are positioned along at least a portion of the subject's spine during use.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
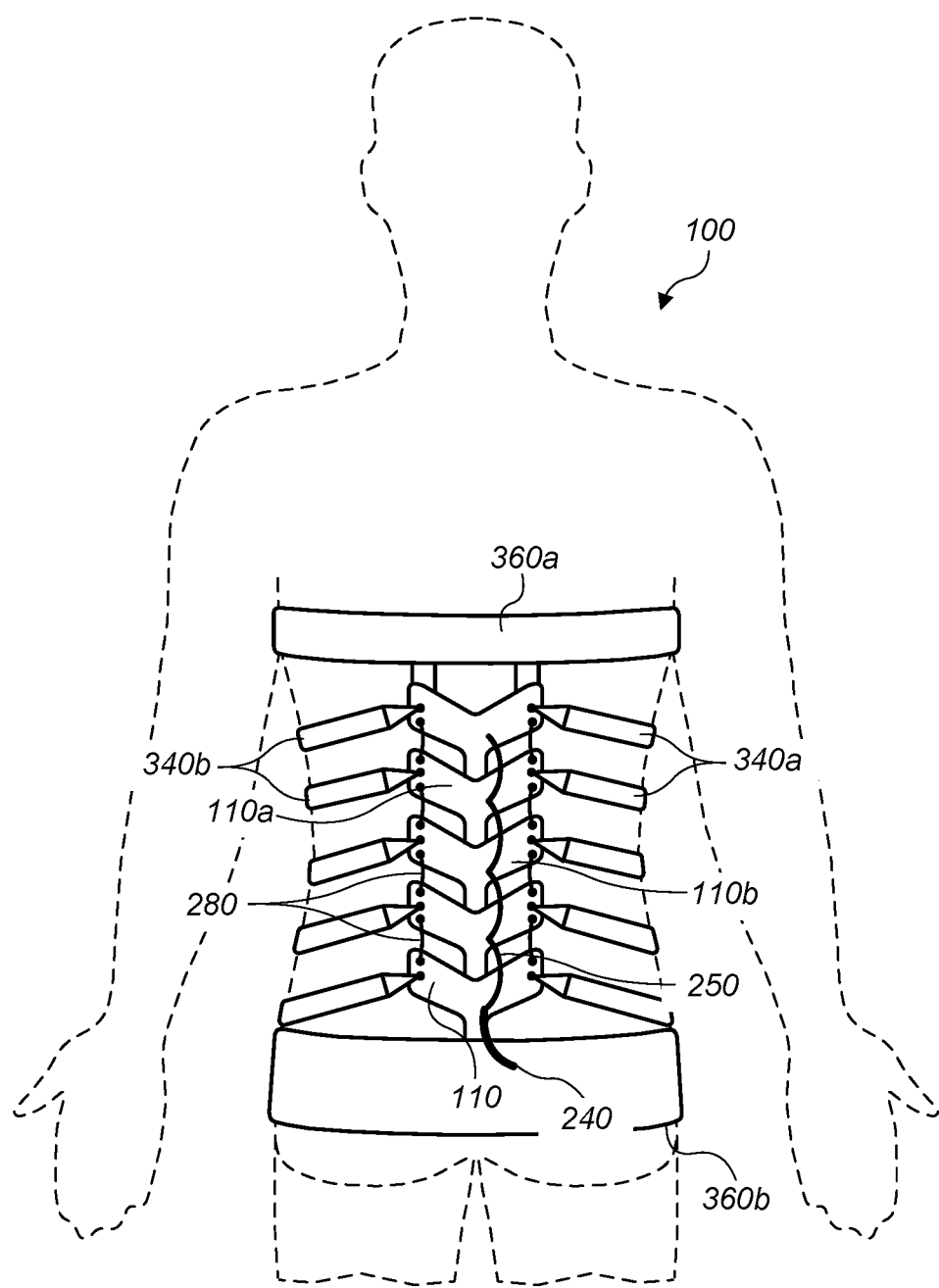
FIG. 1 depicts a rear view of a representation of an embodiment of an external spinal brace system.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. As such, the component can be configured to perform the task even when the component is not currently on.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "elastic" as used herein generally refers to an object or material able to resume its normal shape spontaneously after contraction, dilatation, or distortion.

In some embodiments, a system and/or method may include an external spinal brace system. In some embodiments, the external brace system applies a distraction force to the subject. A distraction force appropriately applied to a subject may overcome abnormal deviations to a subject's spine. This line of reasoning is based at least in part on Hueter-Volkmann Law. The Heuter-Volkmann Law states that compression applied across a growth plate decelerates growth and that tension across a growth plate accelerates growth. This would suggest that applying a distraction force, i.e. tension, to the posterior spine could accelerate the posterior growth of the spine relative to the anterior spine counteracting the development of scoliosis. Wolff's law was developed by the German surgeon Julius Wolff. Wolff's law states that bone in a healthy person or animal will adapt to the loads under which it is placed. If loading on a particular bone increases, the bone will remodel itself over time to become stronger to resist that sort of loading. The internal architecture of the trabeculae undergoes adaptive changes, followed by secondary changes to the external cortical portion of the bone.

Mechanical deviations of the spine may result from anterior overgrowth of spinal vertebrae relative to a posterior side resulting in such conditions as scoliosis. In some embodiments, the external brace system applies a posterior distraction force to the subject. By applying a posterior distraction force bone growth will be encouraged on the posterior side counteracting the anterior overgrowth. In some embodiments, the same principles could be applied when a subject is experiencing posterior overgrowth by applying anterior distraction forces. This may allow a subject who employs an external spinal brace system as described herein to ameliorate or mitigate spinal abnormalities without using surgery or at least reducing the amount of surgical treatments. In some embodiments, an external spinal brace system may provide: axial forces (e.g., resulting in lengthening the spine); lateral forces (e.g., resulting in restricting/ while allowing lateral bending within a predetermined amount (allowing more flexibility than current braces)); compressive forces; and torsional forces (e.g., to counteract rotational forces of, for example, scoliosis).

Figure 2:
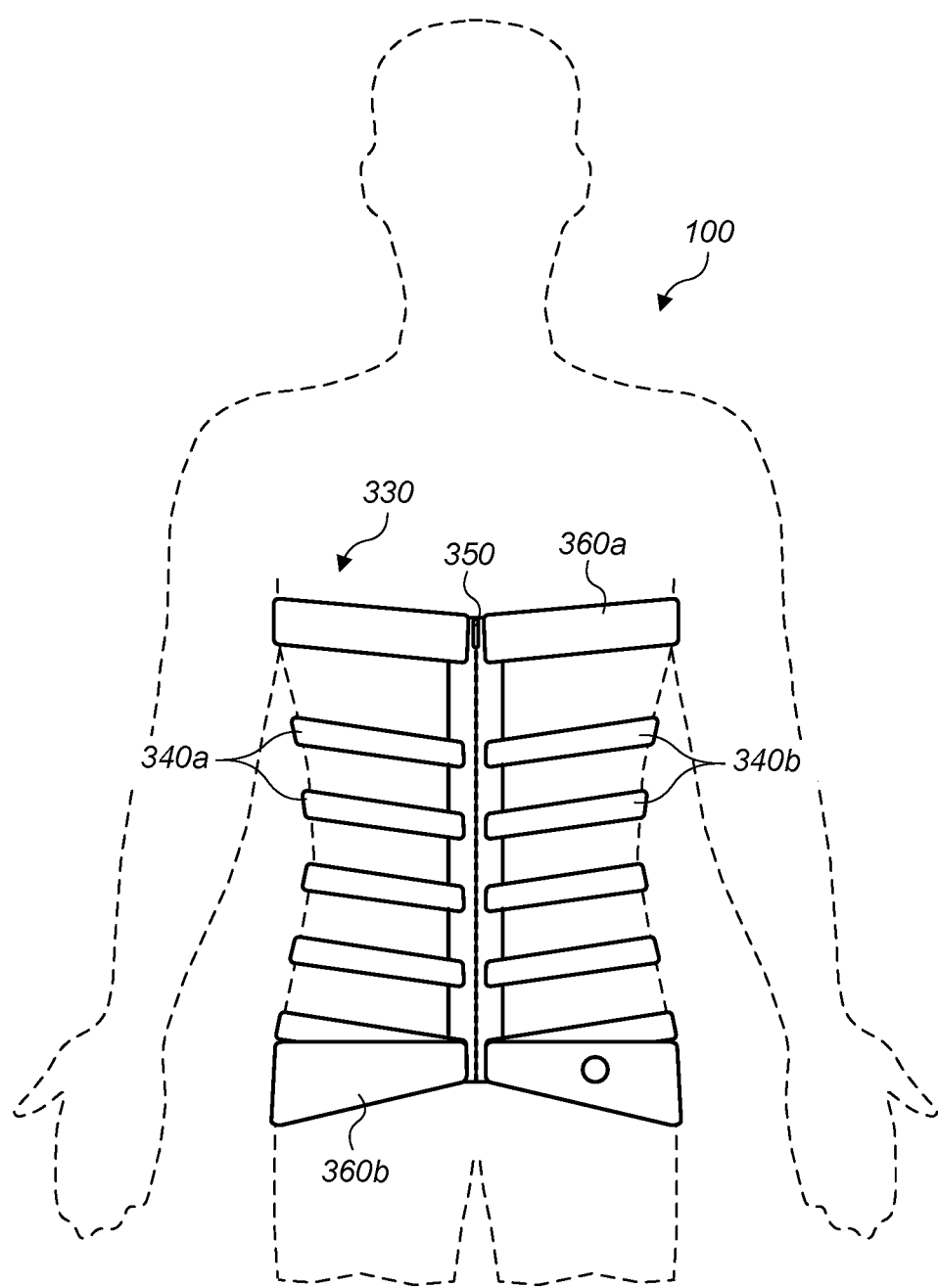
FIG. 2 depicts a front view of a representation of an embodiment of an external spinal brace system.

FIG. 1 depicts a rear view of a representation of an embodiment of an external spinal brace system 100. FIG. 2 depicts a front view of a representation of an embodiment of an external spinal brace system 100. In some embodiments, the system may include a plurality of support mechanisms 110 including at least first 110a and second support mechanisms 110b. The first support mechanism 110a may be coupled (or directly attached), during use, to the second support mechanism 110b such that the first and second support mechanisms are inhibited from decoupling. In some embodiments, the external spinal brace system inhibits spine curvatures in at least several planes of motion comprising lateral bending, flexion, extension, rotation, and ultimately limiting buckling of spine.

Figure 3:
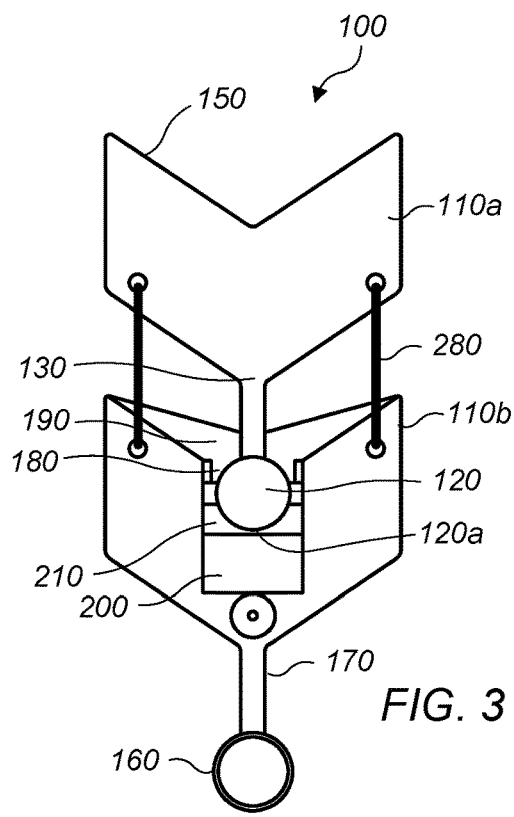
FIG. 3 depicts a rear view of a representation of an embodiment of first and second support mechanism of an external spinal brace system with cut away portions.
Figure 4:
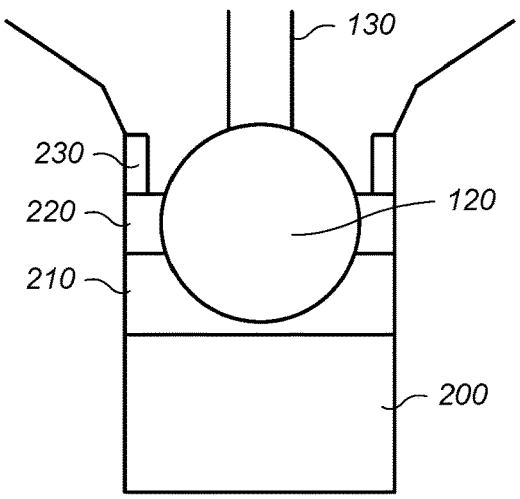
FIG. 4 depicts a rear view of an enlarged representation of an embodiment of the cut away portions from FIG. 3.
Figure 6:
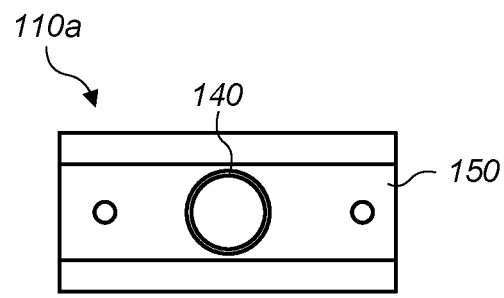
FIG. 6 depicts a top view of a representation of an embodiment of a first support mechanism of an external spinal brace system.

In some embodiments, the support mechanisms may be coupled (or directly attached) together to allow at least limited movement in a subject including, for example, side bending, twist bending, flexion, and/or extension. In some embodiments, the external spinal brace system 100 includes a first coupling portion 120 at a first end 130 of the first support mechanism 110a. The first support mechanism 110a may include a first coupling opening 140 at a second end 150 (e.g., as depicted in FIG. 6) of the first support mechanism (wherein the second end is opposite to the first end of the first support mechanism). The external spinal brace system 100 may include a second coupling portion 160 at a third end 170 of the second support mechanism 110b. The external spinal brace system 100 may include a second coupling opening 180 at a fourth end 190 of the second support mechanism 110b (the fourth end is opposite to the third end of the first support mechanism). The first coupling portion of the first support mechanism is positioned, during use, in the second coupling opening of the second support mechanism such that the first and second support mechanisms are inhibited, during use, from decoupling. FIG. 3 depicts a rear view of a representation of an embodiment of first and second support mechanism 110a-b of an external spinal brace system 100 with cut away portions. In FIG. 3 first coupling portion of the first support mechanism is positioned, during use, in the second coupling opening of the second support mechanism. FIG. 4 depicts a rear view of an enlarged representation of an embodiment of the cut away portions from FIG. 3. Support mechanisms may be formed from lightweight resilient materials that can stand up to the stresses of use and yet not put unwanted stress on the user due to weight. Support mechanisms may be formed at least in part from polymers (e.g. carbon fiber), lightweight metals (e.g., titanium), and/or a combination thereof.

In some embodiments, the first coupling portion 120 may include a substantially spherical portion 120a. The second coupling opening 180 may include a complementary shape to the spherical portion. Complementary spherical portions may allow for various types of movement which may or may not function to mimic normal human movement. Complementary spherical portions may typically function to mimic one or more types of normal human movement allowed by a healthy spine. The coupling may mimic one or more types of normal human movement allowed by a healthy spine while limiting the range of movement in one or more directions based upon the needs of the particular person. For example, a subject with a spinal abnormality such as kyphosis may limit certain human movements which might exacerbate the kyphosis condition. The coupling portions control certain movements of the subject based upon the shapes of the first coupling portion and the second coupling opening. Other means may include stops which limit movement.

In FIGS. 3 and 4 first coupling portion 120 of the first support mechanism 110a is positioned, during use, in the second coupling opening 180 of the second coupling mechanism 110b. Within the opening a resilient member 200 (e.g., fluid chamber, electric, magnetic, or electromagnetic based) may be positioned. A bearing member 210 may be positioned above the resilient member and in some embodiments the bearing member may form a portion of the resilient member. At least one side of the bearing member may include a surface with a complementary surface to at least a portion of the first coupling portion (as depicted in FIG. 4).

In some embodiments, a locking mechanism 220 may function to inhibit decoupling of the first coupling portion from the second coupling opening and as such decoupling of the first support mechanism from the second support mechanism. The locking mechanism may include a lock ring 220. A lock ring is a washer used to prevent components from becoming loose during rotation. In some embodiments, the locking mechanism may include a stop 230 which inhibits movement of the lock ring once assembled and/or positioned in the second coupling opening. The stop may include an expansion stop ring. The locking mechanism 220 and/or the stop 230 may function together or separate to limit certain types of movement of the first support mechanism relative to the second support mechanism.

In some embodiments, the coupling mechanism may include a resilient member 200 which provides a positive distraction force between each support mechanism. The force exerted by the resilient member may be adjustable. In some embodiments, the resilient member may include a spring or elastic member. The spring and/or elastic member may be adjusted by switching out members of different resiliency.

In some embodiments, the resilient member may include a fluid chamber 200. The fluid may exert a distraction force. The fluid may exert a force against a movable plate 210. Fluids may include gasses and/or liquids. As such the force exerted by fluid in the fluid chamber may be adjusted by transferring fluids to or from the fluid chamber. The force may be adjusted employing different types of gasses and/or liquids. The force may be adjusted employing different types of means (e.g., electromagnetic, magnetic, electric, or mechanical (e.g., screw).

Figure 5:
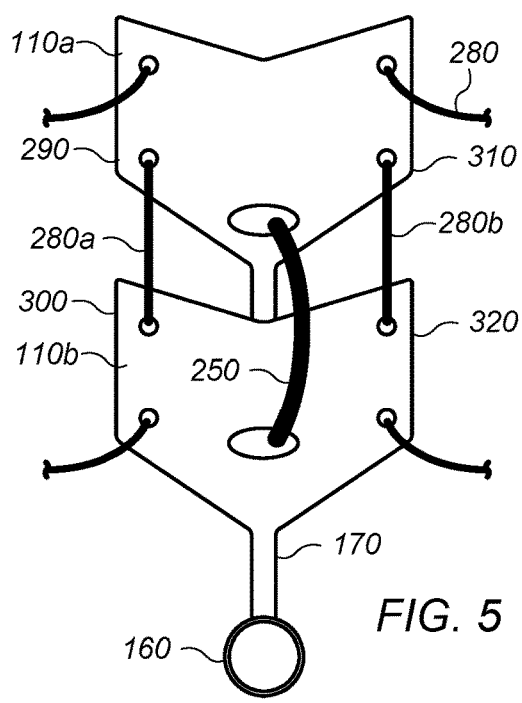
FIG. 5 depicts a rear view of a representation of an embodiment of first and second support mechanism of an external spinal brace system including fluid conduits.

In some embodiments, one or more conduits may be coupled (or directly attached) to the fluid chamber. A first chamber may be coupled (or directly attached) to a fluid source using a conduit 240 (e.g., as depicted in FIG. 1). In some embodiments, each chamber may be coupled (or directly attached) to a fluid source using a conduit 240. In some embodiments, the fluid chambers of an external spinal brace system may be coupled (or directly attached) to each other using a series of conduits 250 (e.g., as depicted in FIGS. 1 and 5 such that only a single fluid chamber needs to be coupled (or directly attached) to a fluid source which is then directed to other fluid chambers through the depicted/discussed conduits).

In some embodiments, as fluid is transferred to the fluid chamber which provides an expansion force against the bearing member moving the bearing member such that a distance between the first support member and the second support member is increased and/or applies a positive distraction force.

Figure 7:
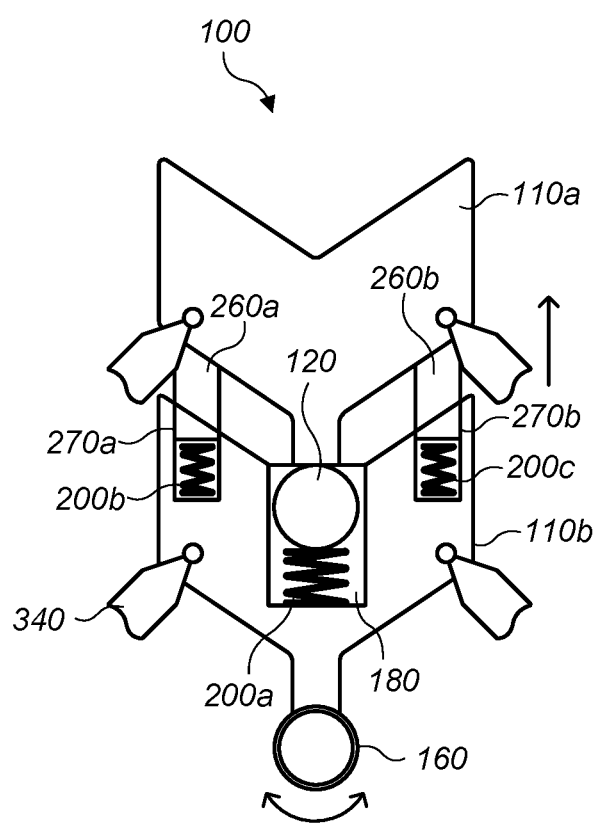
FIG. 7 depicts a rear view of a representation of an embodiment of first and second support mechanism of an external spinal brace system with cut away portions.

FIG. 7 depicts a rear view of a representation of an embodiment of first and second support mechanisms 110a-b of an external spinal brace system 100 with cut away portions. In some embodiments, as described previously herein the first support mechanism 110a may include a first coupling portion 120 as well as a first and a second engaging members 260a-b at a first end of the first support mechanism. The first support mechanism may include a first coupling opening as well as a first and second opening at the second end of the first support mechanism. The second end may be opposite to the first end of the first support mechanism. The second support mechanism 110b may include a second coupling portion 160 at a third end of the second support mechanism 110b. The second support mechanism 110b may include a second coupling opening 180 and a third and fourth opening 270a-b at the fourth end of the second support mechanism 110b. The fourth end may be opposite to the third end of the second support mechanism. The first coupling portion of the first support mechanism may be positioned, during use, in the second coupling opening of the second support mechanism. The first and second engaging members of the first support mechanism may be positioned, during use, in the third and fourth openings respectively of the second support mechanism.

In the embodiment depicted in FIG. 7 resilient members 200a-c are positioned in the second coupling opening 180 and in the third 270a and fourth 270b openings respectively of the second support mechanism. The resilient member which provides a positive distraction force between each support mechanism. The force exerted by the resilient members may be adjustable. In some embodiments, the resilient member may include a spring or elastic member. In the embodiment depicted in FIG. 7 the resilient members are depicted as springs. In some embodiments, one may be able to adjust a spring load using, for example, a screw to increase the load of the spring. In some embodiments, snap rings may be used to keep springs in and/or connect spinal mechanism units, snap rings may allow for a maximum limit of the expansion of the spring.

In some embodiments, the external brace system may include at least one elastic member 280 (e.g., as depicted in FIGS. 1,3,5). The elastic members may function to control (e.g., limit) side (lateral) bending, twist (rotational) bending, flexion and/or extension. The elastic members may be used to assist in correcting abnormal position of a subject's spine. A first elastic member 280a (e.g., as depicted in FIG. 5) may couple (or directly attach) a first side 290 of the first support member 110a to a second side 300 of the second support member 110b. The first side and the second side of the support members may be on the same side of a sagittal plane of the subject. In some embodiments, a second elastic member 280b (e.g., as depicted in FIG. 5) may couple (or directly attach) a third side 310 of the first support member 110a to a fourth side 320 of the second support member 110b. The third side and the fourth side of the support members may be on the same side of a sagittal plane. In some embodiments, the first elastic member and the second elastic member may be on opposing sides of the sagittal plane.

Elastic members 280 may be coupled (or directly attached) on one or more sides of one or more of the support members. By coupling the members to one side as opposed to another may result in different forces on the external brace system and therefore the subject during use. In some embodiments, one or more elastic members are coupled (or directly attached) to a posterior side of the first and second support members. Coupling the elastic members to a posterior surface of the support members may extend one or more portions of the external brace system relative to the wearer. Exerting such a force in such a direction may counteract certain spinal abnormalities such as, for example, hyperkyphosis. Hyperkyphosis refers to the abnormally excessive kyphotic curvature of the spine as it occurs in the thoracic spine. Hyperkyphosis can result from degenerative diseases such as arthritis; developmental problems (e.g., Scheuermann's disease); osteoporosis with compression fractures of the vertebra; tumors or traumatic fractures. In the sense of a deformity, hyperkyphosis is the pathological curving of the spine, where parts of the spinal column lose some or all of their normal profile. This results in relative forward bending of the spine, it can also be seen with poor posture. The first elastic member may exert a first force which is different from a second force of the second elastic member depending upon the needs of the subject.

In some embodiments, one or more elastic members are coupled (or directly attached) to a posterior side of the first and second support members. Coupling the elastic members to an anterior side of the support members may flex one or more portions of the external brace system. Exerting such a force in such a direction may counteract certain spinal abnormalities such as, for example, hyperlordosis. The term lordosis refers to the normal curvature of the lumbar and cervical regions of the spine in the sagittal plane. Excessive curvature of the lower back in the sagittal plane is known as lumbar hyperlordosis.

It should be noted that throughout much of the description herein a first and second support mechanism will be discussed as an example of part of a plurality of support mechanisms. There are no real limits on the number of support mechanisms that may be employed. In fact a typical example of an external spinal brace system may include about 8-20, 12-18, or 15 support mechanisms. The number of support mechanisms may be determined for each individual as needed. The number of support mechanisms may be determined by a user's number of vertebral bodies (e.g., 15 vertebral bodies, T1-L5). The number of support mechanisms may be determined at least in part by the size of the individual support mechanisms and a length of a subject's torso. The number of support mechanisms may be adjusted for a subject as needed (e.g., as a subject grows support members may be added) to reduce costs, as opposed to having to purchase an entirely new external brace system.

In some embodiments, the system may include a coupling system 330 (e.g., as depicted in FIG. 2). The coupling system may couple (or directly attach) the plurality of support mechanisms 110 to a subject such that the plurality of support mechanisms 110 are positioned, during use, along at least a portion of the subject's spine on the surface of the subject. In some embodiments, the coupling system may include a plurality of elongated members 340 coupled (or directly attached) to the plurality of support mechanisms 110. The plurality of elongated members 340 may be coupled (or directly attached) to opposing sides of the plurality of support mechanisms 110. The plurality of elongated members may wrap around the subject in order to couple (or directly attach) the system to the subject during use. A length of the plurality of support members may be adjustable relative to the plurality of support mechanisms. The length may be adjustable using buckles, loops, etc. The ability to adjust the length may be beneficial for sizing the system for each individual subject, for making adjustments to forces applied by the elongated members to treatment as a subject's condition changes. It also allows for adjustments to accommodate growth of a subject.

In some embodiments, the coupling system may include a fastening mechanism 350 (e.g., as depicted in FIG. 2). The fastening mechanism 350 may function to couple (or directly attach) a first portion 340a of the plurality of elongated members to a second portion 340b of the plurality of elongated members (e.g., as depicted in FIG. 2). The first portion 340a of the plurality of elongated members may be coupled (or directly attached) to a first side of the support mechanisms while the second portion 340b of the plurality of elongated members may be coupled (or directly attached) to an opposing second side of the support mechanisms (e.g., as depicted in FIG. 1). In some embodiments, the fastening mechanism may include a zipper, latches, hooks, lacing, hook and loop, snaps, or a combination thereof.

In some embodiments, the system may include one or more coupling elongated members 360 (e.g., similar to a belt) which functions to couple (or directly attach) the system to a subject during use. The coupling elongated members may function to assist in positioning the system relative to the subject during use. An upper elongated member 360a (e.g., as depicted in FIGS. 1-2) may function to couple (or directly attach) the system to an upper portion of a subject. The upper elongated member may be positioned under a subject's armpits or below the subject's shoulder blades. A lower elongated member 360b (e.g., as depicted in FIGS. 1-2) may function to couple (or directly attach) the system to a lower portion of a subject. The lower elongated member may be positioned at a subject's waist at and/or above the subject's pelvis. The coupling elongated members may be formed from substantially flexible and/or rigid materials. In some embodiments, the upper elongated member is positioned, during use, around an upper portion of the subject's torso and the lower elongated member is positioned, during use, around a lower portion of the subject's torso.

In some embodiments, the external spinal brace system provides progressive compressive forces on the ribs for indirect spine correction. Much of the compressive force may be applied by the plurality of elongated members during use. The elongated members may be wrapped around the subject such that as they are tightened (e.g., through use of buckles, adjustment mechanisms, etc.) they exert a compressive force on the subject. The elongated members may provide a compressive force as the support members are separated in order to provide an axial force. In some embodiments, the elongated members may be attached to the support members such that they are oriented down toward a lower portion of the torso (e.g., the pelvis as depicted in FIG. 1), while the support members are attached to the fastening mechanism such that they are oriented up toward an upper portion of the torso (e.g., the shoulder blades as depicted in FIG. 2).

In some embodiments, the external spinal brace system may include bone stimulators which encourage bone growth. Bone stimulators may encourage posterior spinal growth. Bone stimulators may be incorporated directly into the external spinal brace system (e.g., the support members). A variety of biological, mechanical, and physical interventions have been developed to enhance bone growth and fracture healing. There exist a range of physical methods to stimulate bone healing including electrical stimulators, low-intensity pulsed ultrasound, and extracorporeal shock waves. These modalities are less invasive to patients and the cost or complications related to harvesting an autograft are eliminated or at least reduced.

Electrical and electromagnetic (EM) fields are assumed to play a role in bone healing through the same principles as mechanical stress applications. When mechanical load is applied to bone, a strain gradient develops as with Wolff's law. Application of EM to the fracture site is meant to mimic the effect of mechanical stress on bone. A variety of instruments have been are used to deliver electrical and EM fields to fracture sites, including: invasive direct-current (DC) stimulators, noninvasive capacitive coupling (CC) stimulators, and noninvasive inductive coupling (IC) stimulators. The advantages of electrical stimulation may include the low complication rates as compared to other invasive methods. In vitro studies suggest that ultrasonic stimulation enhances bone healing by increasing the incorporation of calcium ions in cultures of cartilage and bone cells and stimulate the expression of numerous genes involved in the healing process. Extracorporeal shock waves (ESWT) have been studied as well for treating bone fractures.

In some embodiments, the external spinal brace system may harness human movement for energy generation for use in the external spinal brace system or for use by other systems. Human movement may be used for energy generation which may be used to power one or more systems of the external brace system and/or stored (e.g., in a rechargeable battery) for later use by one or more external system which are and/or are not associated with the external brace system.

In some embodiments the brace may be used to collect biomechanical data related to human movement and the spine including but not limited to magnitude and force of motion in all planes of movement.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An external spinal brace system, comprising:
    a plurality of support mechanisms, comprising:
        a first support mechanism; and
        a second support mechanism, wherein the first support mechanism is couplable, during use, to the second support mechanism such that the first and second support mechanisms are inhibited, during use, from decoupling;
    a coupling system which is configured to couple, during use, the plurality of support mechanisms to a subject such that the plurality of support mechanisms are positioned longitudinally, during use, along at least a portion of the subject's spine such that the external brace system applies a distraction force longitudinally to the subject.

2. The system of claim 1,
    wherein the first support mechanism comprises:
        a first coupling portion at a first end of the first support mechanism;
        a first coupling opening at a second end of the first support mechanism, wherein the second end is opposite to the first end of the first support mechanism; and
    wherein the second support mechanism comprises:
        a second coupling portion at a third end of the second support mechanism;
        a second coupling opening at a fourth end of the second support mechanism, wherein the fourth end is opposite to the third end of the first support mechanism.

3. The system of claim 2, further comprising a resilient member positioned in the second coupling opening, wherein the resilient member provides a reactive force against the first coupling portion during use.

4. The system of claim 3, wherein the resilient member comprises an expandable fluid chamber.

5. The system of claim 4, wherein the expandable fluid chamber is coupled to a conduit allowing transfer of fluids with the expandable fluid chamber.

6. The system of claim 3, wherein the resilient member is mechanical based, electromechanical based, or viscoelastic based.

7. The system of claim 2, wherein at least a portion of the first coupling portion is positionable in the second coupling opening, and wherein the second coupling opening comprises a shape complementary to the portion of the first coupling portion allowing for the first support mechanism to move relative to the second support mechanism.

8. The system of claim 1, further comprising:
at least one first resilient member coupling a first side of the first support member to a second side of the second support member, wherein the first side and the second side of the support members are on the same side of a sagittal plane; and
at least one second resilient member coupling a third side of the first support member to a fourth side of the second support member, wherein the third side and the fourth side of the support members are on the same side of a sagittal plane, and wherein the at least one first resilient member and the at least one second resilient member are on opposing sides of the sagittal plane.

9. The system of claim 8, wherein the at least one first resilient member exerts a first force which is different from a second force of the at least one second resilient member.

10. The system of claim 1, further comprising:
an upper elongated member configured to couple, during use, the external spinal brace system to the subject; and
a lower elongated member configured to couple, during use, the external spinal brace system to the subject.

11. The system of claim 10, wherein the upper elongated member is configured to be positioned, during use, around an upper portion of the subject's torso, and wherein the lower elongated member is configured to be positioned, during use, around a lower portion of the subject's torso.

12. The system of claim 1, wherein the external spinal brace system functions as a spinal distraction system.

13. The system of claim 1, wherein the external spinal brace system is configured to inhibit spine curvatures in at least several planes of motion.

14. The system of claim 1, wherein the external spinal brace system is configured to inhibit spine curvatures in at least several planes of motion comprising lateral bending, flexion, extension, and rotation.

15. The system of claim 1, wherein the external spinal brace system is configured to provide progressive compressive forces on the ribs for indirect spine correction.

16. The system of claim 1, further comprising at least one resilient member coupling a first side of the first support member to a second side of the second support member, wherein the first side and the second side of the support members are on the same side of a sagittal plane.

17. The system of claim 1, wherein the coupling system further comprises a plurality of elongated members coupled to the plurality of support mechanisms.

18. The system of claim 1, wherein the coupling system further comprises a plurality of elongated members coupled to opposing sides of the plurality of support mechanisms, wherein lengths of the plurality of support members are adjustable; and wherein the coupling system further comprises a fastening mechanism coupling a first portion of the plurality of elongated members to a second portion of the plurality of elongated members.

19. The system of claim 1, further comprising bone stimulators configured to encourage posterior spinal growth.

20. An external spinal brace system, comprising:
a plurality of support mechanisms, comprising:
a first support mechanism, comprising:
a first coupling portion at a first end of the first support mechanism;
a first coupling opening at a second end of the first support mechanism, wherein the second end is opposite to the first end of the first support mechanism; and
a second support mechanism, comprising:
a second coupling portion at a third end of the second support mechanism;
a second coupling opening at a fourth end of the second support mechanism, wherein the fourth end is opposite to the third end of the first support mechanism; and
wherein the first coupling portion of the first support mechanism is positionable, during use, in the second coupling opening of the second support mechanism such that the first and second support mechanisms are inhibited, during use, from decoupling;
a coupling system configured to couple the plurality of support mechanisms to a subject such that the plurality of support mechanisms is positioned along at least a portion of the subject's spine during use.

* * * * *

UNITED STATES PATENT AND TRADEMARK OFFICE
CERTIFICATE OF CORRECTION

PATENT NO. : 11,166,834 B2
APPLICATION NO. : 16/178855
DATED : November 9, 2021
INVENTOR(S) : Ryan C. Murdock It is certified that error appears in the above-identified patent and that said Letters Patent is hereby corrected as shown below:

In the Specification

Column 8:
Line 40, "support members" should be --elongated members--;

In the Claims

Column 12:
Line 17, "support members" should be --elongated members--.

Signed and Sealed this
Eighteenth Day of July, 2023

Katherine Kelly Vidal
*Director of the United States Patent and Trademark Office*